United States Patent [19]

Detty

[11] Patent Number: 5,082,771
[45] Date of Patent: Jan. 21, 1992

[54] DETECTING CELLS USING TELLURAPYRYLIUM DIHYDROXIDES

[75] Inventor: Michael R. Detty, Rochester, N.Y.

[73] Assignee: Eastman Kodak Company, Rochester, N.Y.

[21] Appl. No.: 371,958

[22] Filed: Jun. 27, 1989

[51] Int. Cl.$^5$ .............................................. C12Q 1/10
[52] U.S. Cl. ......................................... 435/38; 435/4; 435/29; 435/34; 435/39; 436/63; 436/164; 436/169; 436/903
[58] Field of Search ................. 436/63, 164, 169, 903; 422/55, 56, 61; 540/1; 435/4, 29, 34, 38, 39

[56] References Cited

U.S. PATENT DOCUMENTS

| | | |
|---|---|---|
| 3,415,718 | 12/1968 | Forkman et al. |
| 4,108,850 | 8/1978 | Fields et al. |
| 4,139,379 | 2/1979 | Chasman et al. |
| 4,144,306 | 3/1979 | Figueras |
| 4,365,016 | 12/1982 | Detty et al. |
| 4,365,017 | 12/1982 | Detty et al. |
| 4,556,636 | 12/1985 | Belly et al. |
| 4,584,258 | 4/1986 | Detty |
| 4,634,553 | 1/1987 | Detty et al. |
| 4,746,607 | 5/1988 | Mura et al. |
| 4,853,186 | 8/1989 | Mura et al. ........................ 436/903 |
| 4,857,271 | 8/1989 | Belly et al. ........................ 422/55 |
| 4,885,240 | 12/1989 | Wu ........................ 422/61 |
| 4,889,797 | 12/1989 | Amano et al. ........................ 422/58 |

OTHER PUBLICATIONS

J. Org. Chem., 1982, 47, 5235.
Organometallic (1988), 7, 1131.
Detty et al., J. Am. Chem. Soc., 1988, 110, 5920–5922.
Guze et al., Am. J. Med. Sci., Dec. 1963, pp. 691–694.

*Primary Examiner*—Robert J. Warden
*Assistant Examiner*—Timothy M. McMahon
*Attorney, Agent, or Firm*—Robert L. Walker

[57] ABSTRACT

A process for detecting the presence of living cells suspended in an aqueous medium preferably at a nearly neutral pH, which comprises:

(a) reducing a tellurapyrylium Te(IV) dihydroxide (TPDH) with cells, optionally while using a substituted benzoquinone electron transfer agent to assist the reduction, thereby producing a change in light absorbance and (b) sensing the change in absorbance to detect or quantify the presence of the cells.

The light absorbance change comprises the appearance of a new spectral peak from the product formed by reduction of the Te(IV) dihydroxide. The new peak has a high extinction coefficient in the near infrared region of the electromagnetic spectrum, i.e., away from the spectral region where some biological components cause spectral interference. Consequently, detection methods provided by this invention have a high degree of sensitivity and are comparatively free from spectral interference caused by materials commonly present in biological materials.

1 Claim, 2 Drawing Sheets

DETECTING CELLS USING TELLURAPYRYLIUM DIHYDROXIDES

CROSS-REFERENCE TO RELATED APPLICATIONS

This application is related to another application filed on the same date, and having U.S. Ser. No. 07/371,960 now U.S. Pat. No. 4,963,669. The related application was filed on behalf of Michael R. Detty (co applicant of this application) and is entitled "Purification of Tellurapyrylium Dyes."

This application is also related to another application filed on the same date, and having U.S. application 07/371,959. The related application is filed on behalf one of the Applicants herein (Michael R. Detty) and is entitled "Detecting Living Cells Using Tellurapyrylium Dihalides."

This application is also related to Belly et al Application Ser. No. 824,766 filed Jan. 31, 1986, and entitled "Reducible Compounds and Analytical Compositions, Elements and Methods Using Same now U.S. Pat. No. 4,857,271."

All of the applications mentioned above are commonly assigned.

1. Field of the Invention

In a preferred embodiment, this invention relates to the detection of living cells, and biological reductants, e.g., enzymes, and reduced flavins. It can be used to determine whether a material to be ingested (e.g., water, milk) is contaminated with microorganisms. It can also be used in technological areas where microorganisms are used to prepare useful products (baking, brewing, and other fermentation arts). It can be used in clinical chemistry to determine the presence of infection (e.g., analysis of blood, urine, and cerebrospinal fluid). The invention has many other fields of use, e.g., protection of the environment (sewage treatment).

The heart of the invention resides in the reducibility of tellurapyrylium Te(IV) dihydroxides with mild reducing agents of the type found in living organisms. The reduction causes a shift in light absorbance, which can be sensed, i.e., measured or detected. This change or shift in light absorbance can be used to determine whether reduction took place, and to what extent.

As stated above, living cells contain mild reducing agents. Using a suitable electron transfer agent when necessary to promote reduction, the reducing agents in such cells can be employed to reduce tellurapyrylium Te(IV) dihydroxides in short reaction times, i.e., up to about 30 minutes. Such reductions can be employed to provide qualitative and quantitative analytical methods for living cells.

Both classes of tellurium compounds involved in the reduction are dyes. In other words, the tellurapyrylium Te(IV) dihydroxides (TPDH), and the products produced on their reduction, are chromophores. Hence, analytical techniques can be based on both materials. However, the reduction products have high extinction coefficients, e.g., greater than 100,000; and up to 300,000 for some species. The peaks with these high extinction coefficients are in the blue to the near infra-red zone of the electromagnetic spectrum. Sensing the change in absorbance in this spectral area provides sensitive analytical methods free of spectral interference from many biological materials. Consequently, the invention provides significant advantages over the prior art. Thus, this invention provides highly efficacious methods for the detection or measurement of living cells (e.g., yeasts, bacteria) in materials suspected of containing such cells. This invention can be extended to the qualitative and quantitative analysis of components of living cells such as enzymes, metabolites, and the like.

Although the process of this invention is primarily directed to the detection of living cells, it can be used to detect dead cells, e.g., by the detection of reducing materials released from the cells. For the latter purpose, one uses longer reaction times to compensate for the slower reduction of the tellurium Te(IV) dihydroxide by non living cells.

Above it was stated that the change in absorbance provided by the formation of the reduction product could be sensed, i.e., detected or measured. This is a preferred technique. However, the decrease in absorbance caused by the diminished amount of the Te(IV) dihydroxide can also be measured, if desired. This expedient can be used where spectral interference by biological constituents is not a problem, and the greater sensitivity of provided by measuring the newly formed peak is not required.

However, it is to be understood that this invention is primarily directed to the sensing if light absorbance caused by the reduction product of the TPDH. As pointed out at various parts of this specification, detection or measurement of the light absorbance resulting from the reduced tellurapyrylium dye has several significant advantages.

For the purpose of this invention, the term "detect" is used in the sense that the presence of an analyte is found or determined, as in qualitative analysis. The term "measure" is used in the sense that the amount of an analyte is determined, as in quantitative analysis.

2. Background of the Invention

Analysis of liquids, such as water, milk and biological fluids is often desirable or necessary for health maintenance and diagnosis. Various compositions and elements to facilitate such analyses are known. Such compositions and elements generally include a reagent composition for determining a substance under analysis, identified as an "analyte" herein. The analyte can be a living organism or a nonliving chemical substance. The reagent composition, upon interaction with the analyte, provides a detectable change (viz, dye formation).

Recently, much work has been directed to developing compositions and elements which are useful for rapid and highly quantitative diagnostic or clinical analysis of biological fluids such as whole blood, serum, plasma, urine and the like.

For example, for the rapid and effective diagnosis and treatment of infectious diseases, it is desirable to be able to detect the ba:teria (or other agent) causing the disease as rapidly as possible. Infections of the urinary tract are among the most common bacterial diseases, second in frequency only to infections Of the respiratory tract. In fact, in many hospitals, urinary tract infections are the most common form of nosocomial infections, often following the use of in dwelling catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 (10³) organisms per ml in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic ba:teriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Current laboratory methods based on culturing microorganisms, e.g., the calibrated loop-direct streak method, require significant incubation periods (18-24 hours) before results can be determined. These laboratory methods are also time consuming to perform and require considerable clinical training and facilities.

Known commercial methods for relatively rapid detection of bacteriuria have serious drawbacks. They are tedious, not completely reliable, require complex reagents or instrumentation, and have limited sensitivity to certain microorganisms and susceptibility to drug or other interferences. Hence, the usefulness of known methods is severely limited.

As can be seen from the above, the detection of living cells is important in many diverse and economically significant fields of interest. Thus, there is always interest in the provision of new methods and materials for such use.

With more specific regard to this invention, Applicants herein provide new analytical methods based on a class of dyes that are non-cytotoxic, or only slightly cytotoxic, to important classes of cells exposed to the conditions employed in this invention. Moreover as stated above, many of the tellurapyrylium materials produced by the process of this invention have high extinction coefficients. Furthermore, as stated above, tellurapyrylium Te(IV) dihydroxides used in this invention give bathochromic shifts upon reduction, yielding product dyes with absorption maxima in the blue to new infrared region of the electromagnetic spectrum, away from spectral interferents (e. g., red blood cells) present in some biological fluids. Hence, this invention presents significant advantages. Analytical methods having such advantages are always of interest in the art.

3. Related Art

Tellurapyrylium dyes are also known as telluropyrylium dyes. Publications describing such dyes, related compounds, and uses thereof are: U.S. Pat. No. 4,365,016; U.S. Pat. No. 4,365,017; U.S. Pat. No. 4,584,258; U.S. Pat. No. 4,634,553; *J. Org. Chem.* 1982, 47, 5235, and *Organometallic* (1988) 7, 1131.

Detty et al, *J. Am. Chem. Soc.*, 1988, 110, 5920-5922, discloses specific TPDH compounds and preparation of one of them by irradiation of an aqueous solution of a Te(II) precursor. That comPound (and another) was also prepared by addition of hydrogen peroxide to aqueous solutions of the Te(II) precursor compounds. The Te(IV) compounds were detected in vitro in cell cultures treated with the Te(II) compounds and light.

It is also known that bacterial microorganisms can reduce dyes, resulting in a colorless product (i.e. dye bleach). Alternatively, colorless materials, e.g. tetrazolium salts, can be reduced to form a colored formazan dye, as described in U.S. Pat. No. 15 3,415,718 (issued Dec. 10, 1968 to Forkman et al) and by Guze et al in *Am. J. Med. Sci.*, Dec., 1963, pp. 691-694. However, the use of formazan dyes for detecting microorganisms has several drawbacks. The formazan dyes generally have low extinction coefficients and therefore cannot be used to detect low levels of microorganisms. The tetrazolium salts have structures that are not readily modified to increase the extinction coefficients of the formazan dyes. Some formazan dyes are insoluble in water and can be toxic to the microorganisms.

U.S. Pat. No. 4,144,306 (issued Mar. 13, 1979 to Figueras) describes a multilayer element for analysis of liquids. This element :an include an interactive composition which interacts with an analyte to release a preformed, detectable moiety from an immobile carrier nucleus upon oxidation or reduction. Such release generally requires the presence of a highly alkaline medium (i.e. pH greater than 13). The spectral absorption band of the preformed detectable moiety is the same before and after release. In other words, the detectable species is not shiftable from one spectral absorption band to another. Therefore, the reference teaches the use of radiation-blocking layers in the element to screen out unwanted absorption from unreleased detectable moiety during the assay.

U.S. Pat. No. 4,108,850 (issued Aug. 22, 1978 to Fields et al) and U.S. Pat. No. 4,139,379 (issued Feb. 13, 1979 to Chasman et al) describe ballasted electron accepting nucleophili: displacement compounds (called BEND compounds therein) which can release dyes or other photographically useful fragments when reduced in the presence of silver halide, an incorporated reducing agent and an electron transfer agent.

U.S. Pat. No. 4,556,636 pertains to the use of indole dyes in the detection of bacteria in specimen samples.

U.S. Pat. No. 4,746.607 relates to the use of substituted quinone electron transfer agents in analytical determinations.

SUMMARY OF THE INVENTION

This invention comprises a process for determining the presence of living cells, said process comprising admixing an aqueous sample suspected of containing said cell, and optionally an electron transfer agent and a nutrient for said cells, and a binuclear tellurapyrylium Te(IV) dihydroxide, at a pH of from about 5 to about 9 for a time sufficient for said Te(IV) dihydroxide to be reduced to a tellurapyrylium dye having a Te(II) moiety, and sensing a change in light absorbance thereby produced to detect the presence of said living cells.

The process is adaptable to either solution or dry assays. A solution assay can be conducted using a porous, absorbent material, e. g., a paper strip containing the reducible Te(IV) compound.

Solution assays can also be conducted by contacting a liquid test sample containing the living cells, with a liquid containing the tellurapyrylium Te(IV) dihydroxide, and preferably an ETA. The ETA can also be mixed with the test sample prior to mixing with the Te(IV) dihydroxide.

If the operator does not require the advantages provided by the ETA, its use can be omitted; for example, the ETA can be omitted when the cell and the dye can interact in such a manner that the TPDH is reduced to a Te(II) reduction product at a satisfactory rate. Whether the reduction rate is sufficiently rapid to obviate the necessity of using the ETA can be determined by routine experimentation.

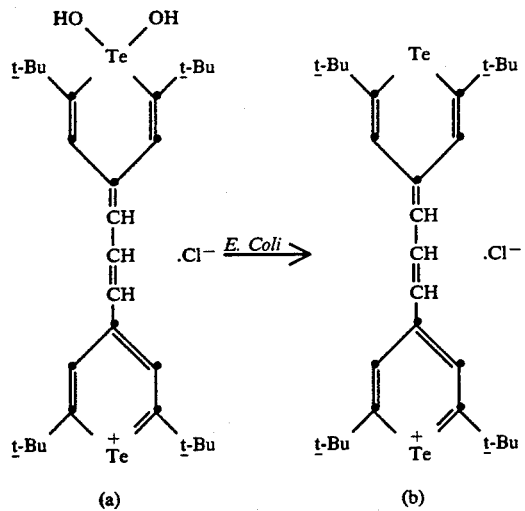

as a function of time.

The original plot is Curve A, and the final tracing is Curve B. As can be seen, the tellurium (IV) dihydroxide has an absorption maximum at about 510 nm and practically no absorption at about 820 nm. Over time, as the E. Coli reduces the tellurium (IV) dihydroxide. i.e., the TPDH. the absorption at 510 nm diminishes until it becomes non existent. As the absorption diminishes at 510 nm, a much more intense absorption peak at about 820 nm arises. In other words, the extinction coefficient for the absorption maximum of the TPDH is much less than the extinction coefficient for the absorption maximum for the reduction product. Stated another way, the extinction coefficient for the absorption peak of the reduction product is much greater than the extinction coefficient for the absorption peak of the TPDH.

Figure 1:
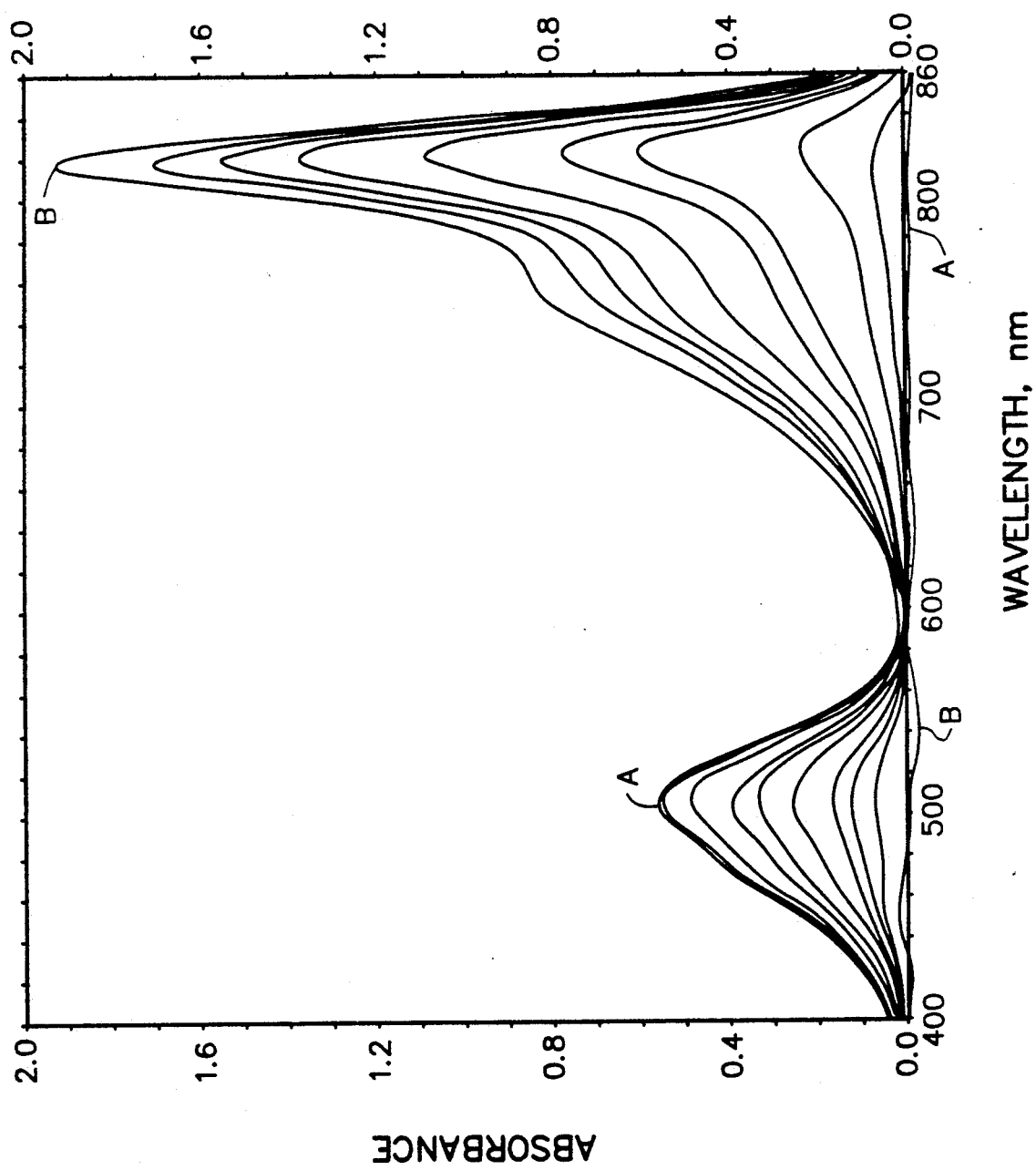
FIG. 1 comprises a series of plots showing the change, over time, of the absorption spectrum of a system comprising E. Coli. and a tellurium (IV) dihydroxide. More specifically, the series of plots follows the reduction.

A skilled practitioner will recognize that FIG. 1 comprises two absorbance spectra; one for a tellurapyrylium Te(IV) dihyroxide useful as an analytical reagent in this invention, and the other for the Te(II) reduction product formed upon reduction of the reagent. Comparison of the two absorption maxima shows the bathochromic shift, i.e., a shift toward the infrared region, which occurs upon reduction. The figure also shows the high extinction coefficient for the peak exhibited by the reduction product.

There is comparatively little absorbance of the TPDH in the region of maximum absorbance of the reduction product. This, and the high extinction coefficient of the reduction product provide for highly sensitive analytical detection of biological cells via (i) a use of the TPDH as an analytical reagent, and (ii) absorbance measurement in the region of maximum absorbance of the reduction product.

The time interval between each spectophometric tracing in FIG. 1 is about 30 seconds.

A name for the TPDH, i.e., compound (a), is 4[3[2,6-bis(1,1-dimethylethyl)-tellurinium -4-yl]-2-propenylidene]-1,1-dihydroxy -2,6-bis(1,1-dimethylethyl)-1,1-dihydro-4H- tellurin chloride.

A name for reduction product (b) is 4-[3-[2,6-bis(1,1-dimethylethyl-4H-tellurin- 4-ylidene]-1-propenyl]-2,6-bis(1,1-dimethylethyl) -tellurinium chloride.

Figure 2:
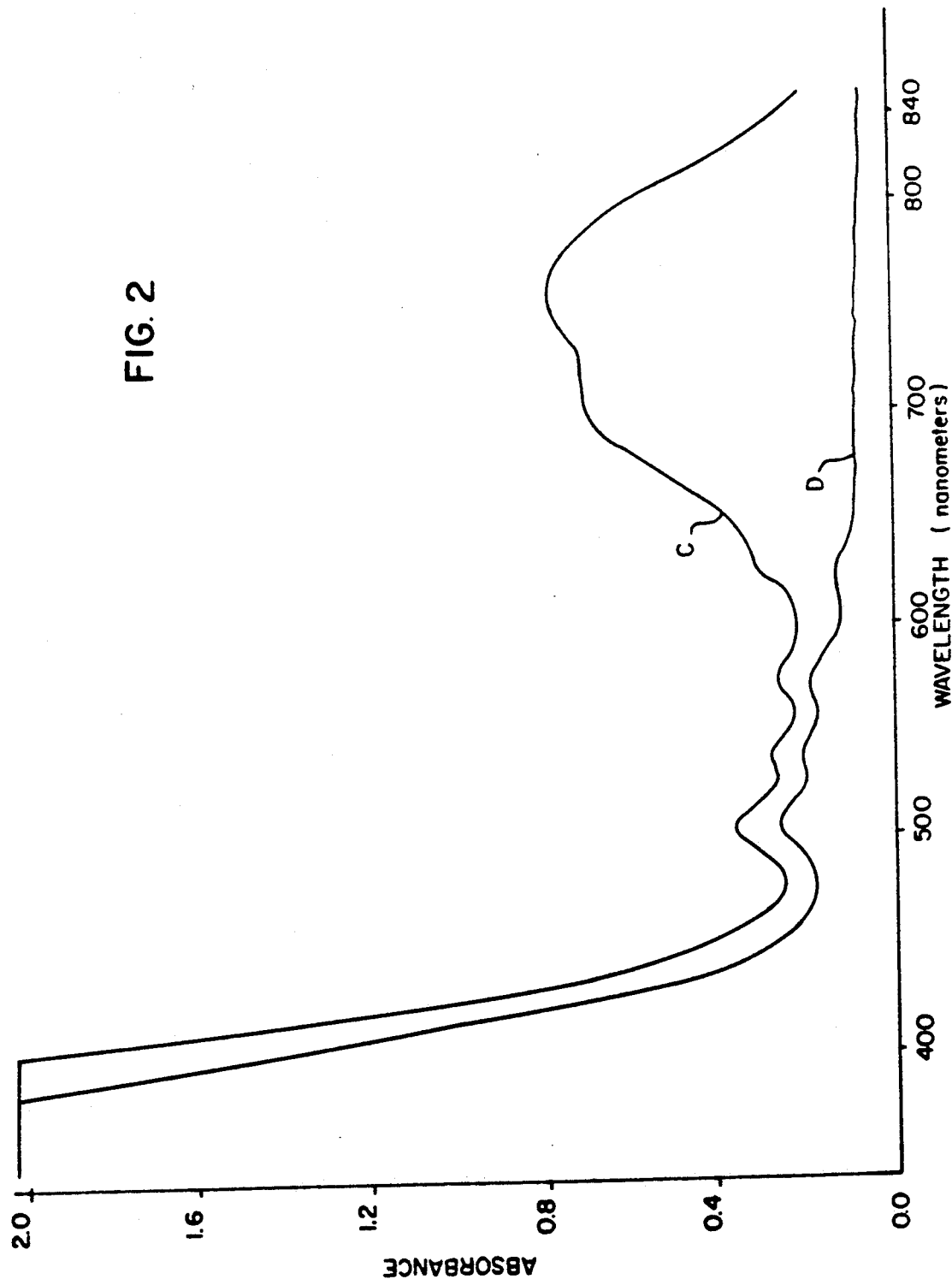

FIG. 2 compares (i) the absorbance spectrum of a compound produced upon mild reduction of a tellurapyrylium Te(IV) dihydroxide, with (ii) a spectrum for a biological fluid (bloody urine). The comparison shows that spectral interference from the biological fluid is in a region away from the absorbance peak of the reduction product.

Stated another way, in FIG. 2, Curve C is the absorbance spectrum for a product formed upon reduction of a TPDH. More specifically, Curve C represents the light absorbance properties of:

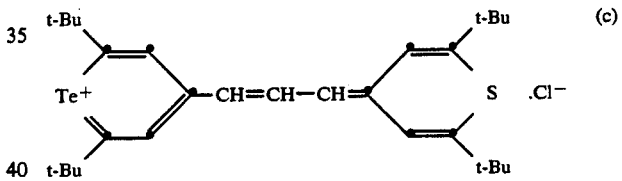

As stated above, Curve D is an absorbance spectrum for a sample of bloody urine. As can be seen by comparison of the curves in the region of 720–780 nanometers, background absorbance from bloody urine is practically insignificant. Hence, compound (c) can be efficaciously employed as an analytical reagent in this spectral region.

Other reduction products of tellurapyrylium reagents, e.g., compound (b), also have absorbance peaks in the spectral region where biological fluids do not absorb light. Hence, the reduction products formed from tellurium (IV) dihydroxides according to the process of this invention can be efficaciously employed in this spectral region.

Comparison of Curves C and D show that bloody urine has a comparatively greater absorbance in the region of about 500-520 nanometers, a spectral region in which measurements have been made when reagents (not within this invention) were employed. Therefore, measurement in the spectral region (e.g., 720-780 nanometers) made possible by this invention has a decided advantage over other methods.

From the figures, it can be seen that the bathochromic shift provided by the reduction of Te(IV) to Te(II) is highly significant for the methods provided by this invention. In this regard, it is significant that no similar bathochromic shift is known for oxygen, sulfur, or selenium analogs of the TPDH reagents used in this invention.

Furthermore, the bathochromic shift employed in this invention was unexpected. There are other sites in the TPDH reagents which are susceptible to reduction. One could expect that reduction at those sites would take place, causing a diminishment in absorbance, rather than an increase in absorbance at another highly useful region of the spectrum.

DESCRIPTION OF PREFERRED EMBODIMENTS

This invention comprises the reduction of a tellurapyrylium compound, in which the tellurium atom is in the +4 oxidation state, to produce a tellurapyrylium compound in which the tellurium atom is in the +2 state. When in the +4, i.e., oxidized state, the tellurium atom is bonded to two hydroxy groups, and to two carbons in the tellurapyrylium ring. In other words, the dihydroxide to be reduced has

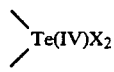

moiety (wherein X represents hydroxy). The reduction product does not have two hydroxy groups bonded to the tellurium atom. That atom, however, remains bonded to two carbon atoms in the tellurapyrylium ring.

The tellurapyrylium Te(IV) hydroxides (TPDH) used in this invention as analytic reagents comprise the ring to which the

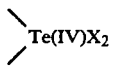

moiety is bonded, and sufficient other organic to provide the desired light absorbing properties. In a preferred embodiment, this additional structure comprises a bridging group, and another ring having unsaturated bonds.

The tellurapyrylium ring containing the Te(IV)X$_2$ moiety is generally bonded to the bridge in a position ortho or para to the Te(IV) atom. Preferably the bridge is in the para position.

The bridge is preferably unsaturated so that it can provide a conjugated double bond system with double bond(s) in the ring containing the

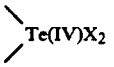

moiety, and to the other ring linked to the bridge.

Thus, this invention can employ tetrapyrylium Te(IV) dihydroxides having the structure:

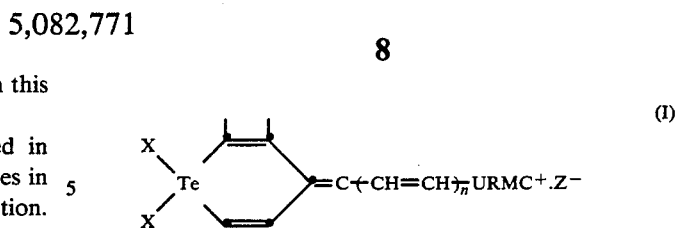

or the structure:

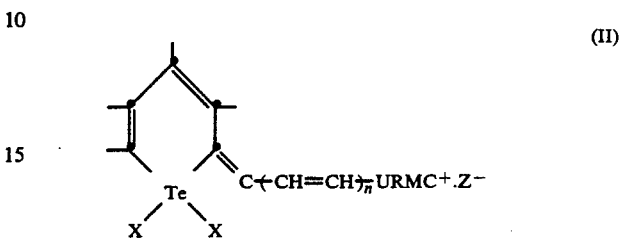

In Formulas (I) and (II), each X is a hydroxy, Z— is a suitable anion, and URMC is an unsaturated ring moiety having double bonds in conjugated relationship with the olefinic double bonds in the bridge,

In the formulas, n is zero or a small whole number, preferably 1 or 2.

In the bridge, each carbon may be bonded to a substituent other than hydrogen. Such substituents may be selected from substituents known for such positions, e.g., alkyl groups and aryl groups having up to about 10 carbon atoms. Preferably, the substituents are hydrogen. When not hydrogen, it is preferred that they be lower alkyl groups; i.e., alkyl groups having up to about four carbon atoms. Preferably such groups are normal, i.e., straight chain, although some branching can be present.

In Formulas (I) and (II), URMC may be a mono or polycyclic heterocyclic or heterocyclylidene alkyl group containing one or more hetero atoms such as O, S, N, P, Se, or Te in rings such as oxazole, oxazolylidene, thiazole, thiazolylidene, selenazole, selenazolylidene, imidazole, imidazolylidene, pyrylium, pyranylidene, thiapyrylium, thiapyranylidene, selenapyrylium, selenapyranylidene, tellurapyrylium, tellurapyranylidene, pyridine, furan, thiophene, selenophene, tellurophene, oxaindolazine, oxaindolazinylidene, and the like or their fused analogs (e.g., benzoxazole, benzoxazolylidene, benzothiazole, benzothiazolylidene, benzopyrylium, benzopyranylidene, benzothiapyrylium, benzothiapyranylidene, benzoselenapyrylium, benzoselenapyranylidene, benzotellurapyrylium, benzotellurapyranylidene, and the like), which may be substituted or unsubstituted; or "URMC" may be an aminoaryl group, ArNR$_8$R$_9$ where Ar is a substituted or unsubstituted, mono- or polycyclic aromatic group and R$_8$ and R$_9$ are alkyl groups, branched or unbranched, or alkyl chains joined to the aromatic ring to form rings (e.g., N,N- dimethylanilino, 9-julolyldyl); or "URMC" may be a carbocyclic aromatic ring, substituted or unsubstituted.

Preferably, URMC is a monoheterocyclic, six membered ring having up to about two hetero atoms. It is also preferred that URMC have two- or three-ring conjugated double bonds in conjugated relationship with the unsaturation in the bridge.

Above it was stated that URMC may be substituted or unsubstituted. The ring containing the

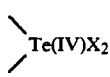

moiety may also be substituted or unsubstituted; in other words, the unsatisfied valences in that ring in Formulas (I) and (II) may all be linked to hydrogen, or one or more of them may be linked to some other substituent.

The substituents present on the rings may be selected from such substituents set forth in the aforementioned U.S. Pat. Nos. 4,365,016; 4,365,017; 4,384,258; and 4,634,553. Preferably the ring substituents are selected from any known substituent which does not interfere with the process of this invention. For the purpose of this invention, such substituents are designated "inert" substituents.

It is preferred that the substituents ortho to Te, Se, S, or O atoms in the tellurapyrylium, selenapyrylium, thiapyrylium, and pyrylium rings be tert-butyl; such substituents make the dyes more stable.

Thus, this invention provides a process for the detection of biological cells in a sample suspected of containing such cells, said process comprising:

(A) reacting said sample with a tellurapyrylium dihydroxide (TPDH) having the formula:

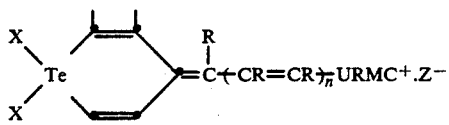
(A)

wherein the tellurium atom is in the +4 oxidation state, each X is hydroxy, each R is independently selected from hydrogen and alkyl and aryl radicals having up to about 10 carbon atoms, n is equal to zero, one, or two, Z is a counterion, and URMC is an unsaturated ring moiety having two or three unsaturated bonds in conjugated relationship with the unsaturation in the bridge

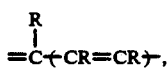

thereby producing a reduction product in which the hydroxy groups are no longer bonded to the tellurium atom and said atom is in the +2 oxidation state, said reduction product having an absorbance maximum in the visible light region more toward the near infrared than the absorption maximum for said TPDH; and (B) sensing the change in absorbance in the region of the absorbance maximum of said reduction product.

Preferably the tellurapyrylium Te(IV) dihydroxides employed in this invention have on of the following formulas:

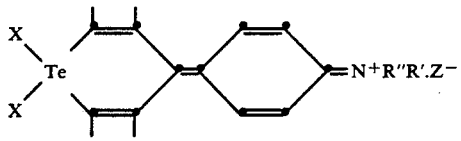
(III)

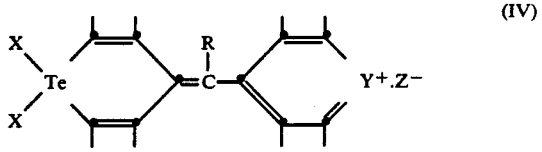
(IV)

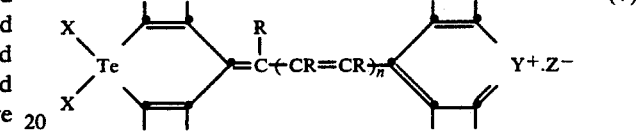
(V)

(VI)

As can be seen, each of the tellurapyrylium Te(IV) dihydroxides illustrated above have the

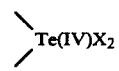

moiety, wherein each X is hydroxide. As stated above, each radical indicated by R is preferably independently selected from the class consisting of hydrogen, or alkyl groups having up to about four carbon atoms. The substituents indicated by R' are independently selected from hydrogen, and alkyl and aryl radicals having up to about 10 carbon atoms.

In a highly preferred embodiment, R is selected from hydrogen and methyl, and R' is selected from hydrogen, methyl, and phenyl. The subscript n in above Formulas (V)–(VI) is equal to a small whole number, more preferably one or two, and most preferably one. Hence. except for those compounds having a nitrogen atom N in conjugation with the $\pi$-framework, it is preferred that the Te(IV) dihydroxide reagents have a methine or a trimethine bridge.

In Formulas (III)–(VI), the rings on the right-hand side of the bridge is a group indicated above by URMC. In Formulas (IV) and (V), Y is a heteroatom, preferably selected from O, S, N, P, Se, or Te. The heteroatoms, S, Se, and Te in the URMC may have a positive charge. The anion Z may be any suitable anion balancing the charge in the tellurapyrylium dihydroxide. Such anions (counterions) may be selected from $BF_4^-$, $ClO_4^-$, $CF_3SO_3^-$, $FSO_3^-$, $PF_6^-$, $CH_3SO_3^-$, $I_3$, $Br_3^-$, $Cl^-$, $Br^-$, $I^-$, and the like.

The unsatisfied valences on the rings in Formulas (III)–(VI) are selected from inert substituents, as discussed above. It is to be understood that pairs of the unsatisfied valences may be linked through bridging atoms or groups to form fused rings.

Thus, in a highly preferred embodiment, the ring with the Te(IV)X$_2$ moiety has one of the following formulas:

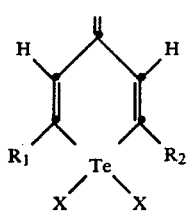

(VII)

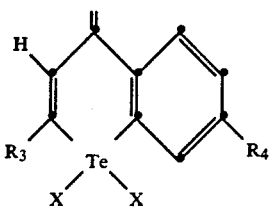

(VIII)

wherein R$_1$ and R$_2$ are hydrogen, alkyl, or aryl radicals having up to about 10 carbon atoms. e.g., methyl, ethyl, iso-propyl, sec-butyl, tert-butyl, and the amyl, hexyl, octyl and decyl groups and so on, phenyl, tolyl, butyl-phenyl, and the life. Of these substituents, hydrogen, methyl, tert-butyl, and phenyl are highly preferred. Preferably R$_1$ and R$_2$ are the same. R$_3$ may be selected from the same groups as R$_1$ and R$_2$. R$_4$ may be selected from such groups and lower alkoxy, e.g., alkoxy groups having one to about four carbon atoms, e.g., methoxy, ethoxy, and the like.

Highly preferred reagents for use in this invention have the formula:

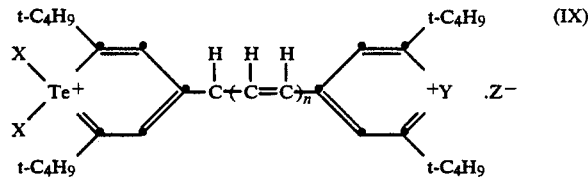

(IX)

wherein X is hydroxy, Y is selected from the class consisting of selenium and tellurium, t-C$_4$H$_9$ is tert-butyl, n is zero or one, and Z is a counterion of the type discussed above.

EXAMPLE 1

The following is a general procedure which was used to prepare aqueous solutions of Te(IV) dihydroxides used as reagents in this invention. Hydrogen peroxide (0.10 mL) was added via syringe to a solution of 1.0 mmol of tellurapyrylium dye in 10 mL of methanol cooled to 0° C. The resulting solution was stirred for 10 minutes. The reaction mixture was poured into 90 mL of cold distilled water or 90 mL of phosphate buffered saline. The aqueous solution was extracted with n-octyl alcohol (2×25 mL). The aqueous solution was filtered through celite to give approximately a 0.01 M solution of oxidized tellurapyrylium dye.

The above procedure was used to prepare tellurium (IV) dihydroxides having formula (IX) in which Y was respectively, tellurium (Te/Te Dye), selenium (Te/S Dye), sulfur (Te/S Dye), and oxygen (TE/O Dye).

For the Te/Te Dye, and Te/Se Dye, $^1$H NMR and other identifying indicia are given below:

For Te/Te: $^1$H NMR (d$_4$-MeOH) δ8.88 (dxd, 1 H J=12.0, 24.8 Hz), 8.68 (s, 2 H), 7.33 (s, 1 H), 7.28 (d, 1 H, J=12.0 Hz), 6.72 (s, 1 H, 1,68 (s, 18 H), 1.52 (s, 9 H), 1.47 (s, 9 H ; λ$_{max}$ (50% aq MeOH, c), nm (56,000). Anal. Calcd for C$_{29}$H$_{45}$O $_{45}$O$_2$Te$_2$.Cl: C, 48.62; H, 6.33. Found: C, 48.60; H, 6.61.

For Te/Se: $^1$H NMR (d$_4$-MeOH) δ8.81 (dxd, 1 H, J=12.0, 15.1 Hz), 8.69 (s, 2 H), 7.36 (s, 1 H), 7.33 (d, 1 H, J=15.1 Hz), 7.07 (d, 1 H, J=12.0 Hz), 6.74 (s, 1 H), 1.65 (s, 18 H), 1.52 (s, 9 H), 1.48 (s, 9 H); λ$_{max}$ (50% aq. MeOH, r), 502 nm (55,000). Anal. Calcd for C$_{29}$H$_{45}$O$_2$-SeTe.Cl: C, 54.79; H, 7.14. Found: C, 55.23; H, 7.35.

The maximum absorption and extinction coefficient for the compounds in water is listed below:

| | |
|---|---|
| For Te/Te Dye: | λ$_{max}^{H2O}$ 510 nm, ε = 56,000 |
| For Te/Se Dye: | λ$_{max}^{H2O}$ 502 nm, ε = 55,000 |
| For Te/S Dye: | λ$_{max}^{H2O}$ 480 nm, ε = 52,000 |
| For Te/O Dye: | λ$_{max}^{H2O}$ 452 nm, ε = 49,000 |

Preparation of other tellurapyrylium Te(IV) dihydroxides can be conducted following the teaching of the above example and the teachings within Detty et al, J. Am. Chem. Soc., 1988, 110, 5920–5922, supra.

The dihydroxy compounds used as reagents in this invention are very soluble in water when compared with other tellurapyrylium dyes. For example, the greater water solubility of the dihydroxy compounds compared to the solubility of analogous dihalo compounds can be demonstrated by the partition coefficient between n-octanol and water. (As well known, the partition coefficient is a measure of the distribution of a substance between two immiscible liquids.) Thus, the partition coefficient of some Te(IV) dihydroxides is in the range of 300–500; this indicates that they are very preferably soluble in n-octanol. On the other hand, the partition coefficient for a dihydroxy analog is typically about (or less than) 0.001, indicating that almost all of the dihydroxy compound stays in the aqueous phase, and very little will enter the Phase. In short, the dihydroxy compounds are very soluble in water and very insoluble in n-octanol, while quite the opposite is true for the dihalo compounds.

The greater water solubility of the dihydroxy compounds makes them better analytical reagents for detecting living cells. More specifically, the dihydroxy compounds can be employed for this purpose by merely dissolving them in water or in an aqueous buffer (in a suitable concentration). On the other hand, the water insoluble dihalo compounds are preferably employed as a dispersion which comprises the dihalo compound, a surfactant, and a water miscible solvent.

Although not necessary, a surfactant can be used with the Te(IV) dihydroxides used as reagents in this invention. More specifically, surfactants which are useful in the practice of this invention include any surfactants which do not inhibit compound reduction. Generally, for detecting of living cells, the useful surfactants are nonionic surfactants, including, for example, alkylarylpolyethoxy alcohols (e.g. TRITON X-100 and X-305 available from Rohm & Haas, Philadelphia, Pennsylvania, U.S.A.), p-alkylaryloxypolyglycidols (e.g. SURFACTANT 10G available from Olin Corp., Stamford, Connecticut, U.S.A.), TWEEN 80 (available from ICI Americas, Inc., Wilmington, Delaware, U.S.A.), and others known to one skilled in the art.

If, desired, the compositions of this invention can contain a water miscible organic solvent, such as alcohols (e.g. methanol, ethanol, propanol, etc.), N,N dimethylformamide, dimethyl sulfoxide, acetonitrile, hexamethylenephosphoramide and the like. Use of such solvents is not required.

The liquid systems used in this invention generally contain a buffer in an amount effective to maintain a nearly neutral pH, i.e., a pH of from about five to about nine. Preferably, the pH is about seven. The concentration of buffer in the dispersion can vary widely, but is generally from about 0.01 to about 0.1 molar. Representative buffers include phosphates, borates and others reported by Good et al in *Biochemistry*, 5, 467 (1966), and *Anal. Biochem.*, 104. 300 (1980).

The stability of the dihydroxycompounds used in this invention is generally very good. For example, it has been demonstrated that at 37° C., the half life of:

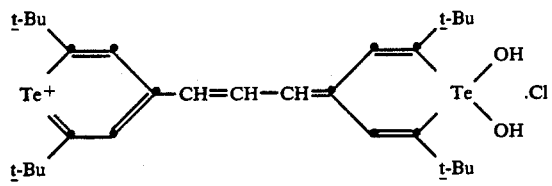

at various pH values is as follows:

| pH | $t_{\frac{1}{2}}$ (hours) |
|---|---|
| 4.58 | 3.5 |
| 5.98 | 4.5 |
| 7.40 | 12 |
| 8.50 | 12 |
| 9.03 | 8.5 |
| 10.20 | 8.0 |
| 11.98 | 6.3 |

The above results indicate that where greater stability is desired, the compound should be used at or near neutral pH.

It has been discovered that the reduction of TPDH compounds used as reagents in this invention can be accelerated by irradiation with light having a wavelength of or about 480 nm in the presence of a protein having histidine or tryptophan as a constituent amino acid. The amount of histidine or tryptophan can be very small, say in a concentration of from about 0.001 M to about 0.1 M. This actinic promotion occurs at ambient and similar temperatures, and can be used to advantage to accelerate the reduction of the dihydroxy compound, and thereby accelerate the chemical change utilized in the analytical methods provided by this invention. To achieve the promotion effect, one irradiates the analytical mixture containing the TPDH and the cell to the extent necessary to provide activation.

Since most microorganisms contain a protein containing histidine and/or tryptophan, this acceleration technique is widely applicable to the analytical methods provided by this invention. Use of the acceleration in reduction rate provided by light a preferred, but non critical embodiment of this invention.

The tellurium (IV) dihydroxides described herein are useful in compositions for analytical determination (i.e. qualitative or quantitative detection) of aqueous and nonaqueous liquids, e.g. biological fluids, manufacturing processes, wastewater, food stuffs, etc. Determinations can be made of various analytes via a single reaction or a sequence of reactions which bring about reduction of the Te(IV) dihydroxide. The various analytes include living cells (e.g. bacteria, white blood cells, yeast, fungi, etc.), enzymes (e.g. lipase, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH based, FADH based or oxidase based assays), biological or chemical reductants other than living cells which will reduce the reducible compound (e.g. ascorbates, cysteine, glutathione, thioredoxin, etc.), metabolizable substances (e.g. glucose, lactic acid, triglycerides, cholesterol, etc.), and immunoreactants (e.g. antigens, antibodies, haptens, etc. which generate reductants).

The compositions can be used to monitor enzyme redox reactions as well as flavin adenine dinucleotide (FAD-FADH) based and nicotinamide adenine dinucleotide (AND-NADH) based and (NADP-NADPH) based reactions. In such instances, the tellurapyrylium Te(IV) dihydroxide can be used to provide a detectable species in place of NADH.

The dihydroxides are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, white blood cells, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

When determining living cells using the tellurapyrylium (Te(IV) dihydroxides, it is preferable to provide for rapid dye formation in such determinations that the living cells interact with an electron transfer agent (herein ETA). The presence of an ETA may also provide more efficient dye release for analytical determinations of nonliving analytes. The ETA is a mobile compound which acts as an intermediary between the substance being determined (e.g. living cell) and the reducible compound. In some instances, the use of an ETA is not required to give usefully rapid dye formation. Hence, the use of an ETA is an optional expedient.

In general, the ETA compounds useful in the Practice of this invention have an $E_{1/2}$ in the range of from about −320 to about +400 mV as measured in aqueous buffer (pH 7) versus the normal hydrogen electrode using a differential pulse polarographic technique with a PAR Potentiostat (Princeton Applied Research, Princeton, New Jersey). In general, the potential of the ETA should be more positive than the potential of the substance to be determined (i.e. analyte) and less positive than the potential of the RIND compound. That is, the ETA should be more easily reduced than the analyte and less easily reduced than the reducible compound. They are generally present at a concentration that is dependant upon the concentration of the analyte, and preferably at a concentrtation of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds useful in the practice of this invention which provide further advantages of low background are those which are the subject of U.S. Pat. No. 4,746,607; supra. In general, those compounds are substituted benzo- and naphthoquinones. The description of such compounds in U.S. Pat. No. 4,746,607, column 3, line 43, to column 8, line 67, is incorporated by reference as if fully set forth. Preferred ETA's have the formula

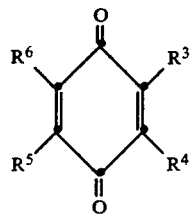

wherein $R^3$ and $R^4$ are independently hydrogen, alkyl, alkenyl, alkoxy, hydroxyalkyl, hydroxyalkoxy, alkoxyalkyl, alkoxyalkoxy, acetoxyalkyl, acetoxyalkoxy, aryl, alkaryl, a heterocycle or a heteroalkyl, and $R^5$ and $R^6$ are independently selected from the substituents defined as $R^3$ or $R^4$, or taken together supply the atoms to complete a 4-to 8-membered fused carbocyclic or heterocyclic ring, provided at least one of $R^3$, $R^4$, $R^5$, and $T^6$ is not hydrogen. Examples of this class of quinones include 2,3-dimethyl-5-hydroxymethyl-1,4-benzoquinone, 2,5-dimethoxy-1,4-benzoquinone, 2,3,5-trimethyl -1,4-benzoquinone, 2,6-dimethoxy-1,4-benzoquinone, 2-hydroxy-methyl-1,4-naphthoquinone and 2-(2-hydroxyethyl)-1,4-naphthoquinone. Preferably the concentration of the ETA is in the range of from about 0.1 to about 100 times the concentration of the TPDH.

The detection of living cells, and particularly of bacterial cells, is often carried out in the presence of a nutrient for those cells although its presence is not essential. Any nutrient media can be used which contains useful metabolizable carbon, and optionally nitrogen, sources. Suitable nutrient media having proper components and pH are well known in the art. Particularly useful nutrients are glucose or tryptose alone or in combination.

The present invention is adaptable to either solution or dry assays. In a solution assay, a solution (or dispersion) containing a tellurapyrylium dihydroxide of the type described above, (TPDH), and optionally an ETA and a nutrient such as glucose, is prepared and contacted with a liquid test sample containing the living cells or analyte to be determined by mixing. The ETA and/or nutrient can also be mixed with the test sample prior to mixing with the reducible compound. Generally the TPDH is mixed with the test sample in a suitable container (e.g. test tube, Petri dish beaker, cuvette, etc.). The resulting solution (or dispersion) is gently mixed and incubated for a relatively short time (i.e. up to about one hour, more preferably 30 minutes) at a temperature up to about 40° C., and generally from about 20 to about 40° C. The test sample is then evaluated by measuring the detectable species, for example, at an appropriate wavelength in the spectral absorption band. Such an evaluation can be done with suitable detection equipment.

A solution assay can also be carried out by contacting a porous, absorbent material, e.g. paper strip, containing the test sample with a dispersion of the TPDH. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Other reagents can be present in amounts readily determined by one skilled in the art.

Alternatively, the method of this invention can be practiced in a dry assay with a dry analytical element. Such an element can be a absorbent carrier material, i.e., a thin sheet or strip of self supporting absorbent or bibulous material, such as filter paper or strips, which contains the TPDH or a dried residue of the dispersion comprising same. Such elements are known in the art as test strips, diagnostic elements, dip sticks, diagnostic agents and the like.

When employed in dry analytical elements, the TPDH compounds described herein can be incorporated into a suitable absorbent carrier material by inhibition or impregnation, or can be coated on a suitable absorbent carrier material. Alternatively, they can be added to the element during an assay. Useful carrier materials are insoluble and maintain their structural integrity when exposed to water or biological fluids such as urine or serum. Useful carrier materials can be prepared from paper, porous particulate structures, cellulose, porous polymeric films, wood, glass fiber, woven and non woven fabrics (synthetic and nonsynthetic) and the like. Useful materials and procedures for making such elements are well known in the art as exemplified by U.S. Pat. No. 3,092,465 (issued June 4, 1963 to Adams et al), U.S. Pat. No. 3,802,842 (issued Apr. 9, 1974 to Lange et al), U.S. Pat. No. 3,915,647 (issued Oct. 28, 1975 to Wright), U.S. Pat. No. 3,917,453 (issued Nov. 4, 1975 to Milligan et al), U.S. Pat. No. 3,936,357 (issued Feb. 3, 1976 to Milligan et al), U.S. Pat. No. 4,248,829 (issued Feb. 3, 1981 to KitaJima et al), U.S. Pat. No. 4,255,384 (issued Mar. 10, 1981 Kitajima et al), and U.S. Pat. No. 4,270,920 (issued June 2, 1981 to Kondo et al). and U.K. Patent 2.052.057 (published Jan. 21. 1981).

A dry assay can be practiced to particular advantage with an analytical element comprising a nonporous support having thereon at least one porous spreading zone as the absorbent carrier material. The TPDH can be in the spreading zone or in a different zone (e.g. reagent zone, registration zone, hydrophilic zone, etc.). The spreading zone can be prepared from any suitable fibrous or non fibrous material or mixtures of either or both. The void volume and average pore size of this zone can be varied depending upon the use intended. For example, if whole blood or other liquid samples containing cells or high molecular weight materials are to be assayed, the void volume and average pore size are generally greater than if serum or urine is to be assayed.

The spreading zone can be prepared using fibrous materials, either mixed with a suitable binder material or woven into a fabric, as described in U.S. Pat. No. 4,292,272 (issued Sept. 29, 1981 to Kitajima et al). From polymeric compositions (e.g. blush polymers) or particulate materials, with or without binding adhesives, as described in U.S. Pat. No. 3,992,158 (issued Nov. 16, 1976 to Przybylowicz et al), U.S. Pat. No. 4,258,001 (issued Mar. 24, 1981 to Pierce et al) and U.S. Pat. No. 4,430,436 (issued Feb. 7, 1984 to Koyama et al) and Japanese Patent Publication 57(1982)-101760 (published June 24, 1982). It is desired that the spreading zones be isotropically porous, meaning that the porosity is the same in each direction in the zone as created by interconnected spaces or pores between particles, fibers, polymeric strands. etc.

The dry analytical element used in this invention can be a single self supporting porous spreading zone containing a reducible comPound and any other desired reagents for a particular use, but preferably such zone is carried on a suitable nonporous support. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g., a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be in a single coated layer. Besides the patents noted above, suitable element formats and components are described also, for example, in U.S. Pat. No. 4,042,335 (issued Aug. 16, 1977 to Clement) and U.S. Pat. No. 4,144,306 (noted above) and Reissue 30,267 (reissued May 6, 1980 to Bruschi).

In the elements of this invention, the amount of the TPDH can be varied widely, but it is generally present in a coverage of at least about 0.01, and preferably from about 0.05 to about 0.2, g/m². Optional, but preferred reagents (e.g. ETA, nutrient, buffer, etc.) are generally present in the following ranges:

| | |
|---|---|
| ETA: | generally at least about 0.001, and preferably from about 0.01 to about 1, g/m², |
| nutrient: | generally at least about 0.05, and preferably from about 0.1 to about 2, g/m² (used only in living cell detection), |
| buffer (pH $\leq$ 9): | generally at least about 0.1, and preferably from about 0.5 to about 2, g/m², and |
| surfactant: | need not be present, but when used, the range is generally at least about 0.1, and preferably from about 0.2 to about 5, g/m². |

One or more of the zones can contain a variety of other desirable, but optional, components, including activators, binders (generally hydrophilic), antioxidants, coupler solvents, etc. as is known in the art, as well as any reagents needed for assay of a particular analyte.

In one embodiment of this invention, an element for detection of microorganisms (e.g. yeast, fungi, bacteria, etc.) in an aqueous liquid comprises an electron transfer agent and a TPDH, both of which are described above. It is desirable that these elements also contain a nutrient for the living cells and a buffer which maintains physiological pH during the assay (e.g. when contacted with a 1-200 µl sample of test liquid). Such an element can be used to detect bacteria, for example, in a urine sample (e.g. one pretreated to eliminate reductive interferents) by physically contacting the sample and element in a suitable manner, and detecting the detectable species released from the reducible compound as a result of the presence of the bacteria at the appropriate wavelength.

In another embodiment of this invention, an element is used for the determination of a nonliving biological or chemical analyte in an aqueous liquid. An interactive composition containing one or more reagents can be incorporated into the element or added at the time of the assay. Examples of such analytes are described above. The amount of detectable species detected can be correlated to the amount of analyte present in the liquid sample.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (e.g. 1-200 µl ) of the liquid to be tested so that the sample mixes with the reagents in the element. Such contact can be accomplished in any suitable manner, e.g., dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

EXAMPLE 2

To demonstrate the utility of the invention, suspension of cells of *E. Coli* having $10^5$ and $10^6$ cells per milliliter were prepared and admixed with appropriate amounts of a stock solution of the (Te/Te Dye of Example 1) in 0.05M phosphate buffer solution having a pH of about 7.8 and a 10% glucose solution. The final concentration of the TPDN was about $1 \times 10^{-4}$ molar after dilution. The reduction of the TPDN reagent by the cells was demonstrated by monitoring the change in optical density (O.D.) at 800 nm as a function of time. Results are set forth in the following table:

The stock solutions of the TPDH can be prepared in a concentration within the range of from about $5 \times 10^{-2}$ and about $5 \times 10^{-4}$ molar.

| $1 \times 10^{-4}$M Te/Te Dye with O.D. measurements at 820 nm. | | | |
|---|---|---|---|
| $10^6$ Cells/mL | | $10^5$ Cells/mL | |
| Time(s)* | Optical Density (O.D.) @ 820 nm | Time(s)* | Optical Density (O.D.) @ 820 nm |
| 0.0 | 0.05 | 0.0 | 0.05 |
| 30 | 0.10 | 60 | 0.15 |
| 60 | 0.32 | 120 | 0.90 |
| 120 | 0.63 | 180 | 0.65 |
| 150 | 0.84 | 240 | 0.89 |
| 210 | 1.15 | 300 | 0.98 |
| 270 | 1.46 | 360 | 1.13 |

-continued

| 1 × 10⁻⁴M Te/Te Dye with O.D. measurements at 820 nm. | | | |
|---|---|---|---|
| 10⁶ Cells/mL | | 10⁵ Cells/mL | |
| Time(s)* | Optical Density (O.D.) @ 820 nm | Time(s)* | Optical Density (O.D.) @ 820 nm |
| 300 | 1.60 | 420 | 1.18 |
| 330 | 1.73 | 480 | 1.23 |
| 390 | 2.00 | 540 | 1.24 |

*Seconds

Following the procedure of the above examples, one may detect or measure the presence of any biological cell in a sample believed to contain such cells. Such cells may be, for example, a pathogenic bacteria or yeast, or a microorganism used for some commercial purpose (e.g., Saccharo mycetaceae). Thus, for example, the process of this invention can be used to detect the presence of the following bacteria which can cause urinary tract infections.

Urinary Tract Infection (UTI)

Microorzanisms
*Staphylococcus epidermidis*
*Enterobacter cloacae*
*Staphylococcus aureus*
*Streptococcus faecalis*
*Klebsiella Dneumoniae*
*Pseudomonas aeruginosa*
*Proteus vulgaris*
*Serratia marcescens*

Good results are obtained when the initial concentration of the cells CFU/ml, is from about $1 \times 10^5$ to about $1 \times 10^7$. Concentrations outside of this range can be used, if desired.

The invention has been described above with particular reference to preferred embodiments thereof. A skilled practitioner familiar with the above-detailed description of the invention can make many modifications and changes without departing from the scope and spirit of the claims that follow.

I claim:
1. A process for the detection of biological cells or biological reductants in a sample suspected of containing such cells or reductants, said process comprising:
   (A) reacting said sample with a tellurapyrylium dihydroxide (TPDH) having the formula:

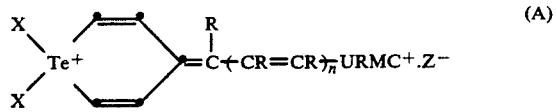

(A)

wherein the tellurium atom is in the +4 oxidation state, each X is hydroxyl, each R is independently selected from hydrogen and alkyl and aryl radicals having up to about 10 carbon atoms, n is equal to zero, one or two, Z is a counterion, and URMC is an unsaturated ring moiety having two or three unsaturated bonds in conjugated relationship with the unsaturation in the bridge

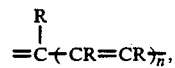

thereby producing a reduction product in which the said hydroxyl groups are no longer bonded to the tellurium atom and said atom is in the +2 oxidation state, said reduction product having an absorbance maximum in the visible light region more toward the near infrared zone than the absorption maximum in said region for said TPDH;
   (b) accelerating reduction of compound (A) by irradiating with light at about 480 nm in the presence of a protein having histidine or tryptophan as a component; and
   (C) sensing the change in absorbance in the region of the absorbance maximum of said reduction product.

* * * * *